(12) United States Patent
Gedouin et al.

(10) Patent No.: US 6,197,303 B1
(45) Date of Patent: *Mar. 6, 2001

(54) UTILIZATION OF NATURAL ALGAE EXTRACTS FOR MAKING A PRODUCT INTENDED TO PREVENT AND CARE FOR DISEASES OF THE SKIN

(75) Inventors: Jean Gedouin; Romuald Vallee, both of Saint-Malo (FR)

(73) Assignee: Codif International S.A., Saint-Malo Cedex (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/842,005

(22) Filed: Apr. 23, 1997

(30) Foreign Application Priority Data

Apr. 26, 1996 (FR) .................................................. 96 05524

(51) Int. Cl.[7] .............................. A61K 35/78; A61K 7/42
(52) U.S. Cl. ......................... 424/195.1; 424/59; 424/123
(58) Field of Search ........................... 424/59, 123, 195.1

(56) References Cited

U.S. PATENT DOCUMENTS 4,822,612 * 4/1989 Shinpo ............................... 424/195.1

FOREIGN PATENT DOCUMENTS

| 2 728 467 | 6/1996 | (FR) . |
| 5062005 * | 5/1980 | (JP) . |
| 0013709 * | 1/1985 | (JP) . |
| 1161208 * | 7/1986 | (JP) . |
| 3135315 * | 6/1988 | (JP) . |
| 2072108 * | 3/1990 | (JP) . |
| 9040523 * | 2/1997 | (JP) . |

OTHER PUBLICATIONS

Database WPI AN 85–208921, IN:Koroleva.
Patent Abstracts of Japan, vol. 14, No. 254.
Patent Abstracts of Japan, vol. 4, No. 98.
Yumeko et al. Medicine and Biology, vol. 127 (3), pp. 213–215, Engl. transl.—pp. 1–6 enclosed, 1993.*
U.S. Court of Appeals Federal Circuit 34 USPQ 2d 1467, Eiselstein v. Frank, 8 pages, 1995.*
Yumeko et al. Med. Biol. (Igaku to Seibutsugaky) vol. 127 (3), pp. 213–215, abstract, 1993.*

* cited by examiner

*Primary Examiner*—Christopher Tate
(74) *Attorney, Agent, or Firm*—Laff, Whitesel & Saret, Ltd.; J. Warren Whitesel

(57) ABSTRACT

The present invention relates to the use of natural extracts of algae for the preparation of a product meant to prevent and to treat skin diseases. The invention also relates to natural extracts of algae meant to prevent and to treat these diseases.

Said use of natural extracts of algae consists in using concentrated extracts of algae of the chlorella type.

The invention especially applies to diseases such as skin rashes or allergic reactions to cosmetic compositions.

2 Claims, 3 Drawing Sheets

UTILIZATION OF NATURAL ALGAE EXTRACTS FOR MAKING A PRODUCT INTENDED TO PREVENT AND CARE FOR DISEASES OF THE SKIN

The present invention relates to the use of natural algae extracts for the preparation of a product meant to prevent and to treat skin diseases, such as skin rashes or allergic reactions to cosmetic compositions. The invention also relates to natural algae extracts meant to prevent and to treat skin diseases.

BACKGROUND

The work of Susuma Tonegawa, Nobel Prize for Medicine in 1987, has shown the immunological function of certain cells of the epidermis, the Langerhans cells, with respect to localized aggressions in the epidermal layer of the skin. The Langerhans cells, that belong to a so-called lymphoid dendritic cell family, essentially are located in the middle layers of the epidermis. Despite their low density, their function is one of information and surveillance over the entire epidermis thanks, especially, to their dendritic nature and to their migratory capability.

The Langerhans cells are capable both of ingesting foreign bodies or allergens that have penetrated into the epidermis, and of transmitting antigens to special immunocompetent cells, the so-called T cells. The activation and protection produced by the Langerhans cells thus make it possible to stimulate the process of intrinsic defense of the epidermis.

Now, it is well known that these cells are directly exposed to ultraviolet rays resulting from exposure to the sun. Recent studies have shown that these radiations to a more or less important extent cause, on the one part, a decrease of the membrane markers, that is to say an alteration of the capability of the presentation of antigens to the immunocompetent cells and, on the other part, a disappearance of the dendrites that characterize the Langerhans cells. In case of extended exposure to the sun, the ultraviolet rays inhibit the Langerhans cells and the latter see their number decrease.

It has been sought to prepare products capable of protecting and of activating the Langerhans cells as a precaution against ultraviolet rays that frequently act on the epidermis.

Thus there are known products prepared from yeast membrane extracts, constituted by polysaccharides of vegetable origin. The products obtained, that are members of the β-1,3 glucanes family, are recognized by the membrane receptors of the Langerhans cells, and it enables these cells to maintain to some extent their macrophagic activity and to protect the immunocompetent cells of the epidermis.

A major drawback of the aforementioned products is found in the relatively high cost associated with their preparation process.

BRIEF DESCRIPTION OF INVENTION

The purpose of the present invention is to propose the use of natural extracts of algae for the preparation of a product meant to prevent and to treat skin diseases, as well as natural algae extracts meant to prevent and to treat these diseases, that are such that said product is obtained by a process relatively simple in execution, that is to say at a moderate cost.

To that end, the use, according to the present invention of natural algae extract for the preparation of the above-mentioned product is characterized in that it consists in using concentrated extracts of algae from the genus Chlorella.

According to another characteristic of the invention, said use of natural extracts of algae is characterized in that these extracts are meant to protect the Langerhans cells of the epidermis from ultraviolet radiations, and to stimulate the development of these cells following the above-mentioned radiations.

According to another characteristic of the invention, these natural algae extracts meant to prevent and to treat skin diseases are such that said algae are from the genus Chlorella.

The above-mentioned characteristics of the invention, as well as others, will appear more clearly upon reading of the following description of one example of execution, this description being given in relation to the attached drawing.

BRIEF DESCRIPTION OF DRAWINGS

The single Figure is a diagram that shows the process for the preparation of an etract from the genus Chlorella according to the invention.

DETAILED DESCRIPTION OF INVENTION

Figure 1:
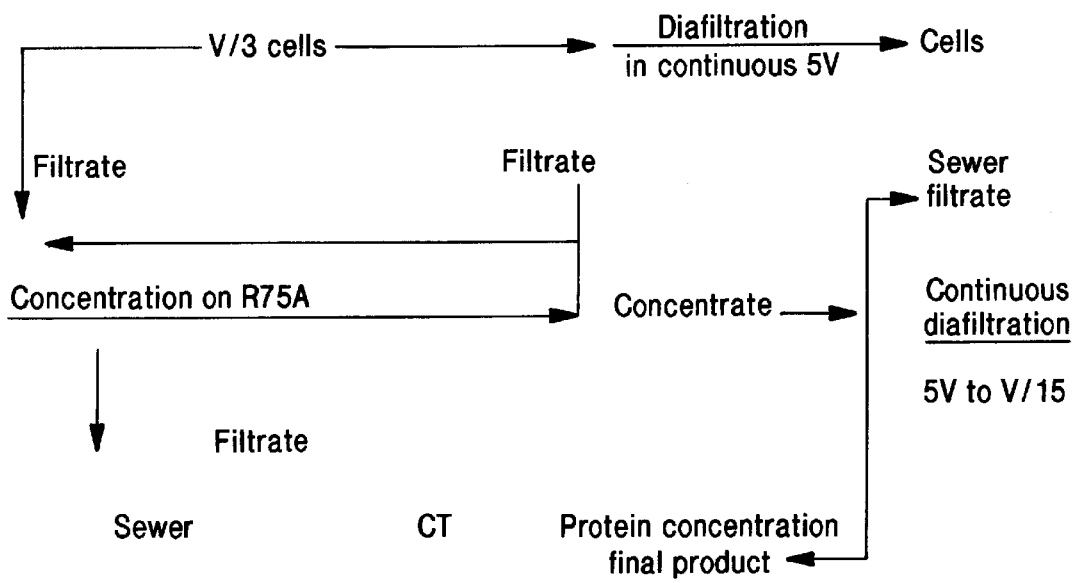
Figure 2:
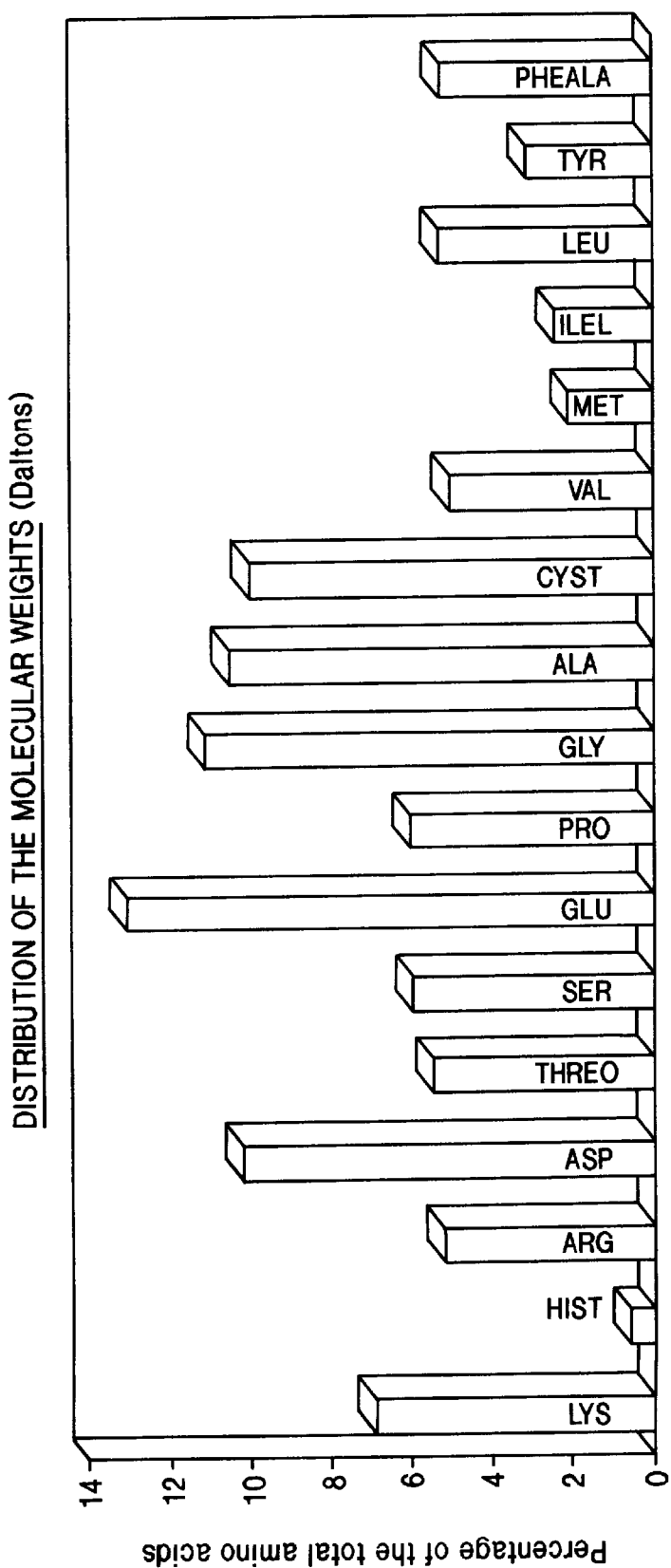
Figure 3:
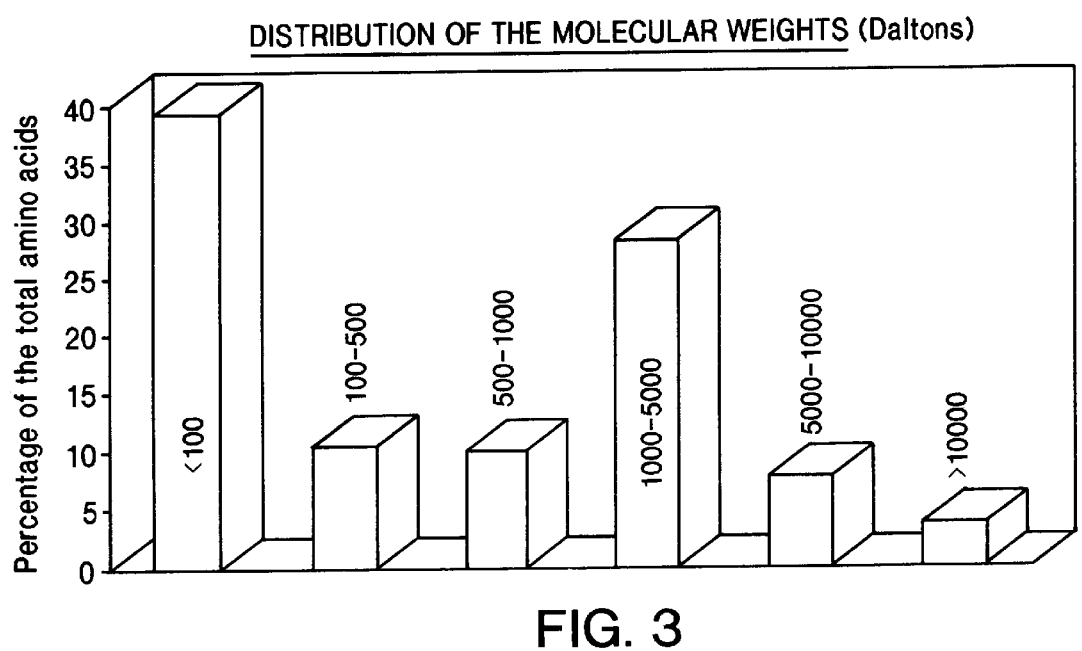

The product according to the invention is prepared from natural extracts of microscopic algae from the genus Chlorella, that are prepared according to the process illustrated in the attached drawings, in which:

FIG. 1 is a flow chart illustrating the inventive process;

FIG. 2 is a bar graph showing the distribution (in percentages) of amino acids in the final product; and FIG. 3 is a bar graph showing the molecular weight distribution of peptides in the final products.

This process essentially consists in performing an alkaline grinding of the algae, in acidifying the extraction juice obtained, in eliminating the cellular wastes (debris) by tangential microfiltration on a filter the retention threshold of which is 0.22 $\mu$m, and in concentrating the remaining organic elements until there is obtained an extract that comprises 5% of active materials, this extract constituting the product according to the present invention.

There are listed below the organoleptic, physicochemical and biological characteristics of the product obtained.

Organoleptic characteristics

Appearance: translucent liquid

Color: light brown-green

Odor: characteristic.

Physicochemical characteristics:

| | |
|---|---|
| pH (20° C.) | 6–7.5 |
| refraction index | 1.30–1.40 |
| Density (20° C.) | > or = to 1 |
| Dry matter (2 g/105° C./2 h | 3–6% |
| Protein content | 1–2.5% |
| Conductivity | 5–15 mS |
| Ashes | 0.75–1.25% |
| Glucide content | 1.75–2.25% |

Bacteriological characteristics:

| | |
|---|---|
| Mesophilic aerobic germs | <100 germs/g |
| Yeasts and molds | <50 germs/g |
| Fecal coliforms | absent in 0.10 ml |
| Total coliforms | absent in 0.10 ml |

-continued

| | |
|---|---|
| Pseudomonas aeruginosa | absent in 0.02 ml |
| Staphylococcus aureus | absent in 0.02 ml |
| Candida Albicans | absent in 0.02 ml |

It must be noted that the high glucide content of the product contributes to its immunomodulating activity.

The graph (FIG. 2) represents the distribution of the total amino acids in the product according to the present invention.

There is observed an important proportion of alanine, of glycine and of proline in the product, which are the main amino-acids of the basic collagen unit. There is also observed an important quantity of lysine that together with proline, are precursors the collagen biosynthesis.

The graph (FIG. 3) shows the molecular weight distribution (expressed in Daltons) of the peptides in the product according to the present invention.

The distribution of the peptides (FIG. 3) shows that 96% of them have a molecular weight less than 10,000 Daltons, There results from this a good potential for the assimilation of the product by the skin.

In order to show the effects of such a product on the epidermis, there was proceeded to an experiment that consists, after radiation by ultraviolet rays of the A class (U. V. A.) in visualizing and in counting the Langerhans cells present in the epidermis, using a fluorescent microscope.

Samples of skin explants from a healthy subject, obtained following a plastic surgery intervention, are placed for survival in a suitable culture medium. Three series of explants are prepared:

the first series, or control series, is such that each explant that constitutes it does not receive the product according to the present invention and is not subjected to U. V. A radiation.

the second series is such that each explant that constitutes it does not receive the products according to the present invention, but is subjected to an U. V. A radiation.

the third series is such that each explant that constitutes it both receives the product according to the present invention, and is subjected to an U. V. A radiation.

The explants of the third series are prepared in the following manner: the product according to the present invention is applied to them twice a day and this for four days. On the fifth day, the product is applied a fifth time TO said explants, that are then subjected to a 7 J/cm$^2$ U. V. A radiation, at the same time as the explants of the second series.

The three series of explants are then frozen by immersion in isopentane that is cooled to −55° C. in liquid nitrogen.

There are then made approximately ten frontal slices of 6$\mu$ inside a cryostat, at a temperature of −16° C., this having as its effect to stop the immunity activity of the Langerhans cells.

There is then proceeded to the incubation of a primary antibody and of a secondary antibody in each explant, which antibodies make it possible to reveal, by means of the immunofluorescence technique, the activity of the Langerhans cells. Indeed, the Langerhans cells are active only when they play an antigenic part by blocking the antibodies, it being possible to observe this antigenic action under a fluorescence microscope.

The primary antibody is chosen so that it recognizes the Langerhans cells, and the secondary antibody, coupled with fluorescent molecules of tetramethyl-rhodamine-isothiocyanate (TRITC) is provided to color these cells.

The cut-up and incubated samples are observed under the fluorescent microscope, so that Langerhans cells that characterize each sample can be visualized and counted.

From 9 to 11 samples were photographed and studied for each series of explants, to make it possible to assess the average number of Langerhans cells per unit of length of the epidermis for the entire group of samples observed. There is also indicated, for each series studied the mean standard deviation (SEM), which is obtained by dividing the typical error obtained by the square root of the number of samples.

The three tables I, II and III below, that respectively relate to three series of implants, give the account of these measurements.

TABLE I

First series of samples:

| Sample | Epidermis in cm | Numb. of Langerhans cells | Numb. of cells/cm |
|---|---|---|---|
| 1 | 18 | 3 | 0.167 |
| 2 | 14 | 5 | 0.357 |
| 3 | 14 | 4 | 0.286 |
| 4 | 17 | 4 | 0.235 |
| 5 | 15 | 4 | 0.267 |
| 6 | 14 | 6 | 0.429 |
| 7 | 16 | 5 | 0.313 |
| 8 | 15 | 8 | 0.533 |
| 9 | 11 | 3 | 0.273 |
| 10 | 15 | 4 | 0.267 |
| MEAN | 15 | 4 | 0.313 |
| SEM | 0.6 | 0.5 | 0.025 |

TABLE II

Second series of samples:

| Sample | Epidermis in cm | Numb. of Langerhans cells | Numb. of cells/cm |
|---|---|---|---|
| 1 | 16 | 4 | 0.250 |
| 2 | 13 | 1 | 0.077 |
| 3 | 22 | 4 | 0.182 |
| 4 | 14 | 4 | 0.286 |
| 5 | 15 | 4 | 0.267 |
| 6 | 15 | 3 | 0.200 |
| 7 | 12 | 3 | 0.250 |
| 8 | 16 | 3 | 0.188 |
| 9 | 17 | 7 | 0.412 |
| 10 | 15 | 2 | 0.133 |
| 11 | 16 | 4 | 0.250 |
| MEAN | 16 | 4 | 0.227 |
| SEM | 0.7 | 0.4 | 0.03 |
| Variation relative to the first series | | | −27% |

TABLE III

Third series of samples:

| Sample | Epidermis in cm | Numb. of Langerhans cells | Numb. of cells/cm |
|---|---|---|---|
| 1 | 16 | 4 | 0.250 |
| 2 | 15 | 5 | 0.333 |
| 3 | 12 | 4 | 0.333 |
| 4 | 13 | 5 | 0.385 |
| 5 | 17 | 7 | 0.412 |
| 6 | 10 | 4 | 0.400 |
| 7 | 16 | 7 | 0.438 |
| 8 | 13 | 5 | 0.385 |

TABLE III-continued

Third series of samples:

| Sample | Epidermis in cm | Numb. of Langerhans cells | Numb. of cells/cm |
|---|---|---|---|
| 9 | 14 | 3 | 0.214 |
| MEAN | 14 | 5 | 0.350 |
| SEM | 0.7 | 0.4 | 0.024 |
| Variation relative to the second series | | | +54% |
| Variation relative to the first series | | | +12% |

When comparing the respective results obtained for the first two series, there is seen that the number of Langerhans cells decreses by 27% following an U.V.A. radiation.

When comparing the results obtained for the third series with those obtained for the first two series, respectively, it is seen that the explants treated with the product according to the invention, then irradiated with U.V.A., contain 54% more Langerhans cells, relative to the explants of the second series, that was irradiated but not treated. It will also be noted that these explants treated and irradiated contain 12% more Langerhans cells than the explants of the first control series, the controls in which the cells are neither treated nor irradiated.

The product according to the invention thus exerts a protective action, and especially a stimulating action on the Langerhans cells contained in the epidermis, following a radiation of the latter with ultraviolet rays. Consequently, the macrophagic activity of these cells is increased and the protection of the epidermis against external aggressions is improved.

It will be noted that exposure of the epidermis to ultraviolet rays constitutes a simple test that makes it possible to validate the immunomodulating activity of the product according to the invention. It would also be possible to use to that end a test that doses the I-α interleukins, for example.

What is claimed is:

1. A therapeutically active topical composition for protecting epidermal Langerhans cells against ultraviolet radiation and stimulating the development of said cells after said radiation, said composition comprising an effective amount of a concentrated Chlorella extract, whereby the concentrated Chlorella extract is prepared by:

(a) alkaline grinding the Chlorella algae to form a juice;
   (b) acidifying the juice of step (a);
   (c) microfiltering the juice of step (b); and
   (d) concentrating the filtrate of step (c) to form a concentrated Chlorella extract.

2. A method of protecting and of stimulating the Langerhans cells of the epidermis comprising the step of topically applying an effective amount of a composition comprising an active concentrated extract of algae from the genus Chlorella combined with a pharmaceutically acceptable carrier, wherein the concentrated Chlorella extract is in an amount effective to protect epidermal Langerhans cells from ultraviolet radiation and to stimulate development of said cells after said radiation, whereby the concentrated Chlorella extract is prepared by:

(a) alkaline grinding the Chlorella algae to form a juice;
   (b) acidifying the juice of step (a);
   (c) microfiltering the juice of step (b); and
   (d) concentrating the filtrate of step (c) to form a concentrated Chlorella extract.

* * * * *